United States Patent [19]

Solazzi

[11] Patent Number: 5,630,989

[45] Date of Patent: *May 20, 1997

[54] APPARATUS FOR TRIMLESS SAMPLE CUP USED IN X-RAY SPECTROSCOPY

[75] Inventor: Monte J. Solazzi, Jupiter, Fla.

[73] Assignee: Chemplex Industries, Inc., Stuart, Fla.

[*] Notice: The term of this patent shall not extend beyond the expiration date of Pat. No. 5,451,375.

[21] Appl. No.: 696,104

[22] Filed: Aug. 13, 1996

Related U.S. Application Data

[63] Continuation of Ser. No. 440,644, May 15, 1995, abandoned, which is a continuation of Ser. No. 292,058, Aug. 17, 1994, Pat. No. 5,451,375.

[51] Int. Cl.$^6$ ................................................ G01N 23/10
[52] U.S. Cl. ........................................ 422/102; 422/104
[58] Field of Search ................................ 422/101, 102, 422/104; 436/171, 177, 174

[56] References Cited

U.S. PATENT DOCUMENTS

| | | |
|---|---|---|
| 2,127,397 | 3/1938 | Freedlander . |
| 4,046,138 | 9/1977 | Libman et al. . |
| 4,148,732 | 4/1979 | Burrow et al. . |
| 4,184,360 | 1/1980 | Vadnay et al. . |
| 4,256,474 | 3/1981 | Berger, Jr. et al. . |
| 4,301,010 | 11/1981 | Eddleman et al. . |
| 4,362,047 | 12/1982 | vonReis et al. . |
| 4,402,909 | 9/1983 | Solazzi . |
| 4,409,854 | 10/1983 | Solazzi . |
| 4,643,033 | 2/1987 | Solazzi . |
| 4,665,759 | 5/1987 | Solazzi . |
| 4,698,210 | 10/1987 | Solazzi . |
| 4,961,916 | 10/1990 | Lesage et al. . |
| 4,982,615 | 1/1991 | Sultan et al. . |
| 5,451,375 | 9/1995 | Solazzi ............................ 422/102 |

*Primary Examiner*—Lyle A. Alexander
*Attorney, Agent, or Firm*—Plevy & Associates

[57] ABSTRACT

A sample receptacle for retaining a sample that is to be subjected to spectrochemical analysis. The sample receptacle includes a tubular body having at least one open end and a tapered exterior wall. A sheet of thin film material having peripheral edges is disposed across the open end of the tubular body. A generally annular collar, having an interior wall tapered at an angle supplemental to the taper of the interior wall, is disposed around the tubular body. As the annular collar is placed around the tubular body, the tapered exterior wall of the tubular body creates an interference fit with the tapered interior wall of the annular collar. The tapered surfaces of the tubular body and the annular collar engage the sheet of thin film material and pull the sheet of thin film material taut over the open end of the tubular body. The annular collar is sized to engage the entire length of the exterior wall of the tubular body. The portions of thin film material not covering the open end of the tubular body, including the peripheral edges of the thin film material are compressed between the tapered exterior wall of the tubular body and the tapered inside wall of the annular collar. As such, the sample receptacle can be handled without having to trim extraneous thin film material from the sides of the tubular body.

20 Claims, 3 Drawing Sheets

APPARATUS FOR TRIMLESS SAMPLE CUP USED IN X-RAY SPECTROSCOPY

This is a continuation of application Ser. No. 08/440,644, filed on May 15, 1995, entitled METHOD AND APPARATUS FOR TRIMLESS SAMPLE CUP USED IN X-RAY SPECTROSCOPY now abandoned which is a Continuation-in-Part of prior application Ser. No. 08/292,058, filed on Aug. 17, 1994, now 5,451,375, issued Sep. 19, 1995.

FIELD OF THE INVENTION

This invention relates to a sample cup for use in holding specimens for spectrochemical analysis, and more particularly to a sample cup comprised of a collar that pulls a thin film material taut over the open end of cell body, thereby obstructing one end of the cell body and creating the sample cup. The collar engages the thin film material in a manner that eliminates the need to trim the thin film material, thereby increasing the efficiency by which sample cups can be prepared.

BACKGROUND OF THE INVENTION

Spectroscopy is the science where a sample substance is analyzed by means of the spectra of light the sample absorbs or emits. Technological advancements in both wavelength-dispersive (WD-XRF) and energy-dispersive (ED-XRF) X-ray fluorescence instrumentation enable the spectroscopic analysis of virtually all types of sample materials. In this technology, sample cups or sample receptacles are employed to hold or contain liquid, solid and powdered specimens. Many conventional prior art sample cups consist of four components. The four components include a cell body with at least one open end; a thin film of material capable of covering the open end of the cell body; an annular collar used to pull the thin film of material taut over the open end of the cell body; and a snap-on ring used to secure the thin film of material in place. The thin film of material encloses a sample substance within the cell body and provides a sample surface plane which is exposed to an excitation source, such as an X-ray tube, during the spectrochemical analysis. Such conventional prior art cups are exemplified by U.S. Pat. No. Des. 238,693 entitled "CELL FOR X-RAY SPECTROSCOPY OR SIMILAR ARTICLE" issued on Feb. 3, 1976 to Monte J. Solazzi; U.S. Pat. No. 4,409,854 entitled "SAMPLE CUP WITH VENTING MEANS FOR USE IN X-RAY SPECTROSCOPY" issued on Oct. 18, 1983 to Michael C. Solazzi; U.S. Pat. No. 4,643,033 entitled "SAMPLE CUP FOR USE IN X-RAY SPECTROSCOPY" issued on Feb. 17, 1987 to Monte J. Solazzi; U.S Pat. No. 4,665,759 entitled "SAMPLE CUP WITH A CANTILEVER BEAM VENTING MEANS" issued on May 19, 1987 to Monte J. Solazzi; and U.S. Pat. No. 4,698,210 entitled "SAMPLE CUP APPARATUS FOR USE IN X-RAY SPECTROSCOPY EMPLOYING SELECTIVELY OPERATED VENTING MEANS" issued on Oct. 6, 1987 to Michael C. Solazzi. All of the above patents are assigned to Chemplex Industries, the assignee herein.

During spectrochemical analysis it is essential for the surface of thin film material, which covers the opened top of the cell body, to remain planar in order to produce reliable data. The area of the thin film material that covers the top of the cell body, is known as the sample surface plane. During the spectrochemical analysis of certain specimens that exhibit a high abrogation in air, the sample cup retaining the specimen may be placed within a vacuum or inert gas environment. Under conditions where pressure equalization is not implemented, the thin film of material covering the sample will distend or bow outwardly due to the differential in pressures between the area within the sample cup and the environment surrounding the sample cup. This places portions of the thin film of material closer to the source of excitation. This variation in distance from the sample plane to the source of excitation alters the intensity of the characteristic radiation of the specimen and also alters the intensity of radiation impinging upon the sample specimen from the excitation source. Consequently, the spectrochemical analysis may produce erroneous quantitative data. For applications in a gaseous environment where pressure is greater on the outside of the sample cup than within the sample cup, the thin film of material distends or is drawn into the hollow of the sample cup providing a concave sample surface. This effect increases the distance between the sample plane and the excitation source and results in erroneous analytical data.

In order to equalize pressure and eliminate distension of the sample surface plane, some sample cups are provided with a venting means. The venting means may be activated to provide pressure equalization between the inside and outside of the cup. Other sample cup designs include a main cell component with both ends opened. This double open-ended cup allows for attachment of the thin film sheet prior to the introduction of the sample. This design is useful for applications in an environment where continuous venting is desired from the moment of sample introduction.

In the prior art, when a sheet of the thin film material is positioned over the open end of a cell body by means of the annular collar, portions of the thin film of material extend beyond the collar along the outer walls of the cell body. This excess portion of the thin film of material has a tendency to flare away from the sides of the cell body and impairs the handling of the sample cup. As such, the excess thin film material must be trimmed from the sides of the cell body in order that the sample cup may be conveniently handled.

Furthermore, in the prior art, securing the thin film of material over the open end of the cell body is a two step process. First, the annular ring must be placed over the thin film of material so as to pull the thin film of material down along the sides of the cell body. Second, the snap-on ring must be applied to secure the thin film of material into place. The two step operation causes excessive manipulation of the thin film of material which often results in the ripping of the thin film of material as the thin film of material is repeatedly stressed against the cell body.

It is therefore an object of the present invention to provide an improved sample cup including a single piece snap-on collar designed to retain a thin film of material over the open end of a cell body, without having any portion of the thin film material extend beyond the snap-on collar. Such a design eliminates the need to trim extraneous thin film material from around the cell body. This simplifies sample cup preparation by reducing operational steps and labor required to assemble the sample cups.

It is also an object of the present invention to provide a sample cup which eliminates wrinkles in the thin film of material which covers the opened end of the cell body. The wrinkle-free thin film of material provides a consistently planar sample surface. Specially designed edges on the cell body prevent inadvertent tearing of the thin film sample support material during its attachment.

SUMMARY OF THE INVENTION

The present invention is a sample receptacle for retaining a sample that is to be subjected to spectrochemical analysis.

The present invention sample receptacle includes a tubular body having at least one open end and a tapered exterior wall. A sheet of thin film material having peripheral edges is disposed across the open end of the tubular body. A generally annular collar, having an interior wall tapered at an angle supplemental to the taper of the interior wall, is disposed around the tubular body. As the annular collar is placed around the tubular body, the tapered exterior wall of the tubular body creates an interference fit with the tapered interior wall of the annular collar. The tapered surfaces of the tubular body and the annular collar engage the sheet of thin film material and pull the sheet of thin film material taut over the open end of the tubular body. The annular collar is sized to engage the entire length of the exterior wall of the tubular body. The portions of thin film material not coveting the open end of the tubular body, including the peripheral edges of the thin film material, are compressed between the tapered exterior wall of the tubular body and the tapered inside wall of the annular collar. As such, the sample receptacle can be handled without having to trim extraneous thin film material from the sides of the tubular body.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Figure 1:
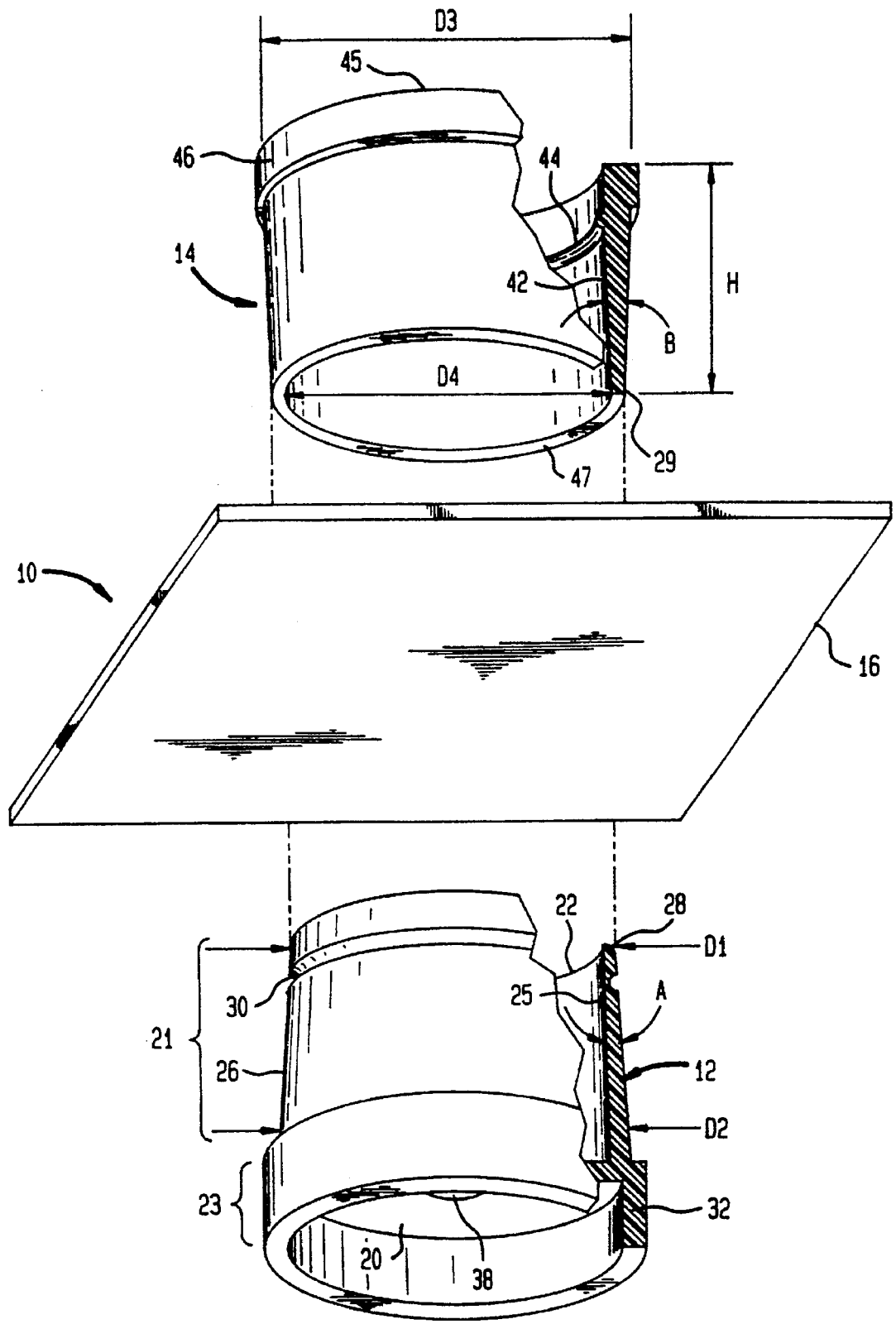
FIG. 1 is an exploded perspective view of a first exemplary embodiment of a sample cup according to the present invention.

Referring to FIG. 1, there is shown one preferred embodiment of a sample cup or receptacle 10 according to the present invention. The sample cup 10 consists of three members, that include a main cell body 12, a thin film material 16 and an annular collar 14 designed to secure the sheet of thin film material 16 over the cell body 12.

The cell body 12 includes a sample retaining region 21 and a reservoir region 23. The sample retaining region 21 of the cell body 12 is tubular in shape having an open end 22 and a closed end 20. The inner wall 25 of the sample retaining region 21 is generally cylindrical and extends in the vertical direction from the closed end 20 up to the open end 22. As such, the inner wall 25 defines a hollow 18, capable of retaining a sample specimen (not shown). The outside wall 26 of the sample retaining region 21 is tapered at an angle of inclination A. The outside wall 26 tapers toward the end 22 of the sample retaining region 21. As such, the outside wall 26 has a first diameter D1 at the open end 22 that is smaller than the second diameter D2 at the closed end 20 of the sample retaining region 21. The edge 28 of the outside wall 26, proximate the open end 22, is rounded. Furthermore, a continuous semicircular groove 30 is disposed in the outside wall 26 proximate the edge 28.

The taper of the outside wall 26 ends at the interface of the sample retaining region 21 and the reservoir region 23. The reservoir region 23 is comprised of a cylindrical wall 32, having a vertical inside and outside surface, that surrounds and extends below the closed end 20 of the sample retaining region 21. A venting provision 38 may be disposed within the closed end 20. The venting provision 38 may be optionally ruptured, thereby allowing the hollow 18 of the sample retaining region 21 to communicate with the reservoir region 23. As such, any sample contained within the sample retaining region 21 can be vented to the reservoir region 23 as is currently practiced in many sample cups of the prior art.

A sheet of thin film material 16 is positioned over the open end 22 of the cell body 12. The thin film material 16 is flexible and transparent to the radiant energy used in the spectrochemical analysis. The possible compositions of such thin film materials 16 are well known in the art and need not be set forth herein at length.

An annular collar 14 is used to properly position the thin film material 16 across the open end 22 of the cell body 12. In the preferred embodiment, the annular collar 14 has a vertical height H that is at least as high as the sample retaining region 21 on the cell body 12. The annular collar 14 is generally tubular having first open end 45 and second open end 47. The annular collar 14 has an interior wall 42 which is tapered at an angle of inclination B that is supplementary to the angle of inclination A on the outside wall 26 of the sample retaining region 21 of the cell body 12. The interior wall 42 tapers toward the second open end 47. As such, the first inner diameter D3 of the annular collar 14, proximate the first open end 45, is larger than the second inner diameter D4, proximate the second open end 47. The interior wall 42 has a rounded edge 29 proximate the second open end 47 that faces the interior of the annular collar 14. A continuous semicircular protrusion 44 extends inwardly from the interior wall 42 proximate the first end 45 of the annular collar 14. A lip extension 46 is disposed on the exterior of the annular collar 14. The lip extension 46 facilitates the handling and the alignment of the overall sample cup 10 when assembled and placed within spectroscopic instrumentation.

Figure 2:
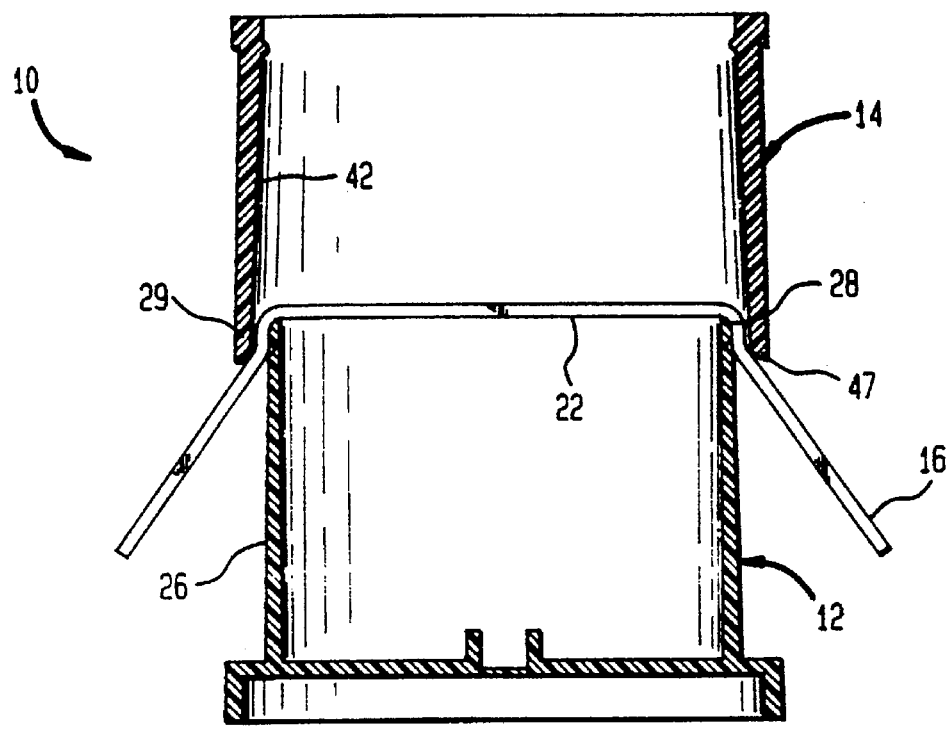
FIG. 2 is a cross-sectional view of the exemplary sample cup embodiment of FIG. 1 shown in a partially assembled configuration.

Referring to FIG. 2, it can be seen that as the annular collar 14 is advanced over the cell body 12, the thin film material 16 becomes pinched between the outside wall 26 of the cell body 12 and the interior wall 42 of the annular collar 14. As such, as soon as the second open end 47 of the annular collar 14 passes the open end 22 of the cell body 12, an interference fit occurs between the annular collar 14, thin film material 16 and cell body 12. Consequently, the thin film material 16 is immediately pulled taut across the open end 22 of cell body 12. As the annular collar 14 is further advanced along the cell body 12, the thin film material 16 is then pulled taut over the edge 28 of the outside wall 26 on the cell body 12. The rounded shape of the edge 28 prevents the thin film material 16 from being torn by the cell body 12. Similarly, as the annular collar 14 is advanced, the thin film material 16 is pulled across the edge 29 of the interior wall 42. The rounded shape of the edge 29 prevents the thin film material 16 from being torn by the annular collar 14.

As the annular collar 14 is advanced along the cell body 12, the interference fit between the interior wall 42 of the annular collar 14, the thin film material 16 and the outside wall 26 of the cell body 12 increases due to the tapered shapes of both the interior wall 42 and the outside wall 26. As the forces of the interference fit increase, the tautness applied to the thin film material 16 increases, thereby eliminating any folds or wrinkles in the portion of the thin film material 16 covering the open end 22 of the cell body 12.

Figure 3:
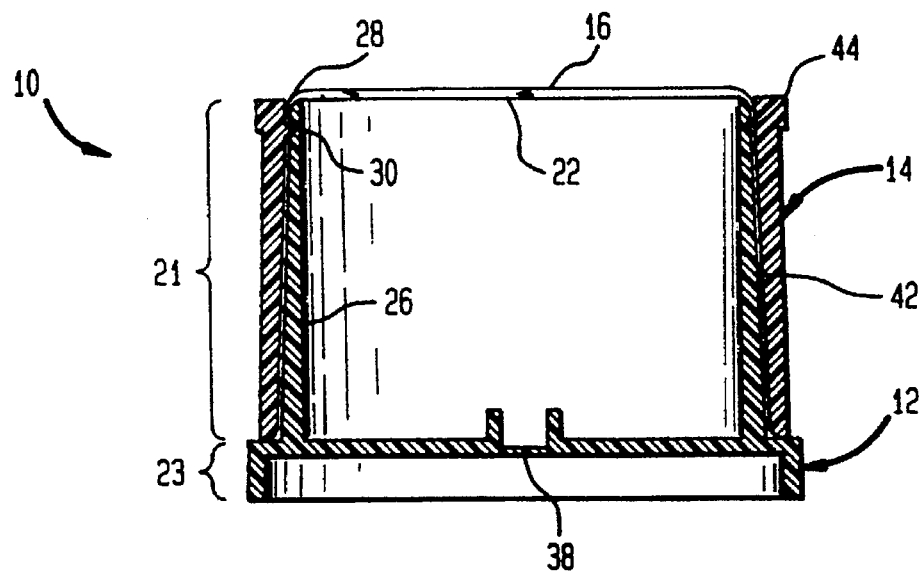
FIG. 3 is a cross-sectional view of the exemplary sample cup embodiment of FIGS. 1 and 2 shown in an assembled configuration.

Referring to FIG. 3, it can be seen that the annular collar 14 completely engages the entire length of the sample retaining region 21 of the cell body 12 when the sample cup 10 is fully assembled. Assembly of the sample cup 10 is completed once the annular collar 14 is advanced far enough over the cell body 12 so that the semicircular protrusion 44 on the interior wall 42 of the annular collar 14 fits into the semicircular groove 30 on the outside wall 26 of the sample retaining region 21. Completion of assembly is indicated by a characteristic "snap" as the semicircular protrusion 44 coacts with the semicircular groove 30.

Once the sample cup 10 is assembled, the thin film material 16 is drawn tightly over the open end 22 of the cell body 12. The thin film material 16 creates a seal over the edge 28 of the cell body 12 which is impermeable to the sample contained therein. The interference fit between the tapered interior wall 42 of the annular collar 14 and the tapered outside wall 26 of the sample retaining region 21 of the cell body 12 occurs for the entire length of the annular collar 14. This prevents any loosening of the thin film material 16 that covers the opened end 22 of cell body 12. As such, the thin film material 16 will remain taut over the open end 22, creating a wrinkle-free sample surface plane for the spectrochemical analysis.

As mentioned, the interference fit between the annular collar 14 and the cell body 12 occurs over the entire length of the tapered surfaces. Any thin film material 16 not coveting the open end 22 of the cell body 12 is compressed between the outside wall 26 of the sample retaining region 21 and the interior wall 42 of the annular collar 14. Provided an appropriate length of thin film material 16 is initially used, none of the thin film material 16 will extend beyond the length of the annular collar 14. Thus, the step of having to trim extraneous portions of thin film material 16 away from the exterior of the sample cup 10 is eliminated. Use of the sample cup 10 with the one-piece annular collar 14 greatly simplifies sample preparation since the number of operational steps are reduced.

Any time after the sample cup 10 is assembled, the sample substance may be subjected to spectrochemical analysis. This will normally require inverting the sample cup 10 so that the open end 22 of the main cell body 12 is facing downward. At that time, any substance contained within the sample cup 10 will come in contact with the portion of thin film material 16 covering the open end 22 of the sample retention region 21. The sample is then ready for analysis.

If venting is required during analysis of the sample contained within the sample cup 10, the venting provision 38 may be optionally ruptured with a blunt device for maintaining pressure equalization within the hollow 18 of the sample cup 10 and the X-ray optics environment. Venting of the sample cup 10 allows the thin film material 16 to maintain a planar sample surface over the open end 22 of the sample retaining region 21 by eliminating inward or outward distension under positive inert gas pressure and in an evacuated condition, respectively. The reservoir region 23 collects any temperature sensitive fluid sample substances having tendencies to expand during analysis.

The main cell component 12 and the annular collar 14 are preferably fabricated from unrecycled natural polyethylene. This eliminates the potential possibility of introducing metallic contamination that may adversely affect the analysis of a sample substance. Polyethylene is one of a number of thermoplastic materials that can be utilized in this application because of its excellent mass attenuation properties encompassing the 1 to 12 Angstrom analyte wavelength range. In addition, polyethylene is resistant to chemical attack, temperature softening, and degradation from excitation energy sources, as well as exhibiting excellent tensile strength for adequate sample retention.

Figure 4:
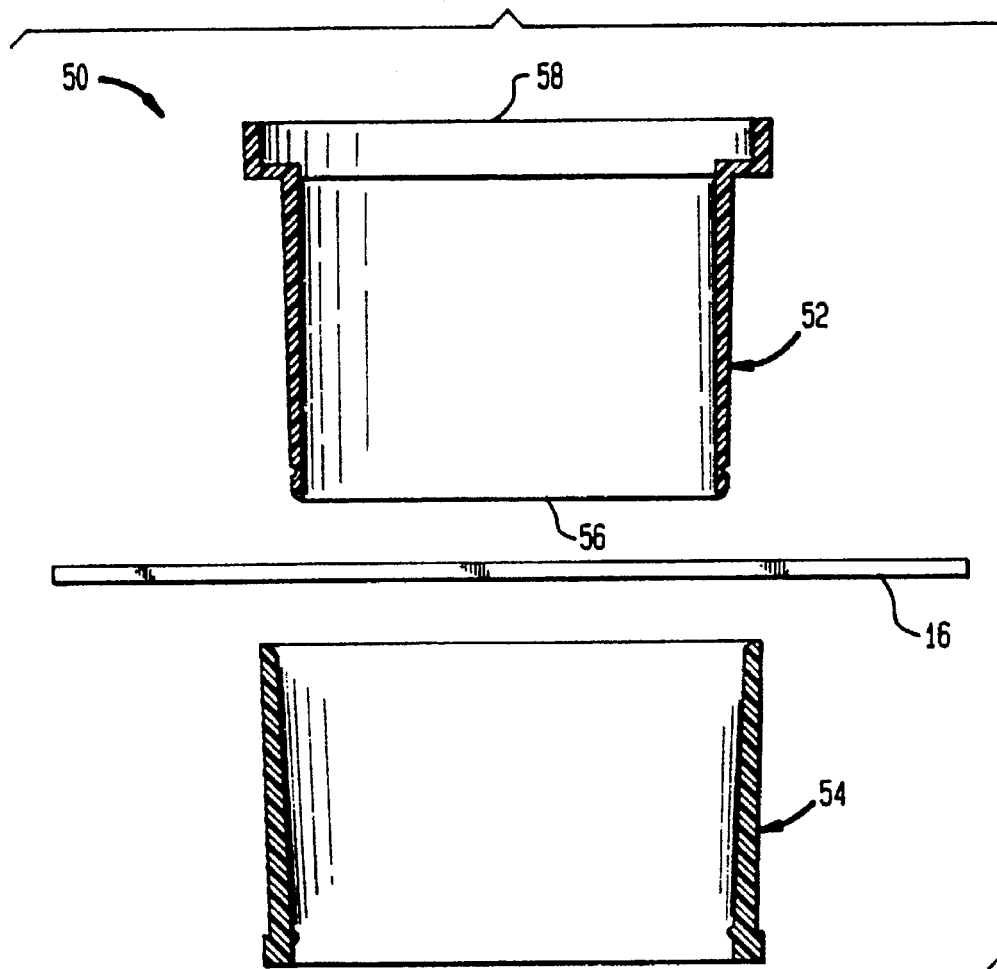
FIG. 4 is an exploded cross-sectional view of an alternate embodiment of the present invention sample cup.

Referring to FIG. 4, a second preferred embodiment of a sample cup 50 according to the present invention is shown. The sample cup 50 consists of three members, and includes a main cell body 52, a thin film material 16 and annular collar 54 designed to secure the sheet of thin film material over the cell body 52. The cell body 52 includes a first open end 56 and a second open end 58. Other than the fact that both ends 56, 58 of the cell body are open, the sample cup 50 is identical to the sample cup 10 shown in FIGS. 1–3. Consequently, the annular collar 54 fits over the cell body 52 to secure the sheet of thin film material 16 in the manner previously described.

Figure 5:
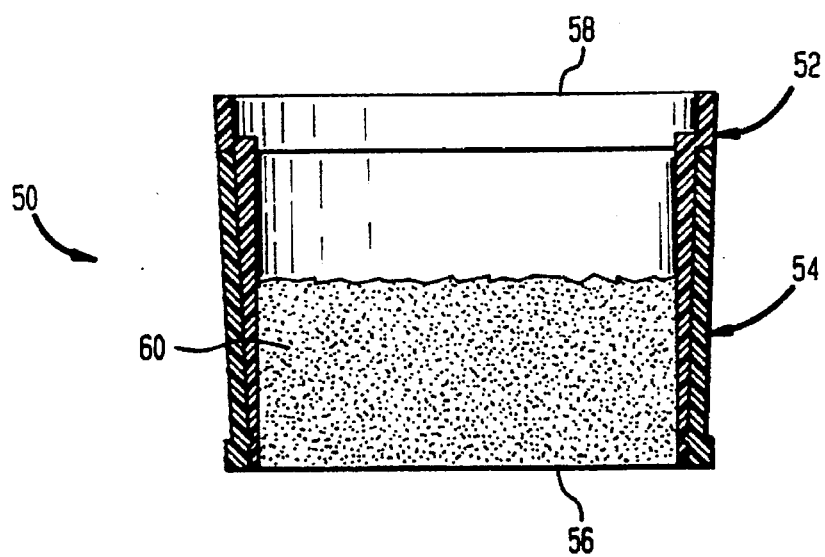
FIG. 5 is a cross-sectional view of the alternate embodiment of FIG. 4, shown in an assembled configuration.

Referring to FIG. 5, the assembled sample cup 50 is shown with a sample substance 60 contained therein. The second open end 58 of the cell body 52 remains open even after the sample cup 50 is assembled. As such, the sample substance 60 located within the sample cup is always equalized to the pressure of the ambient environment. The sample substance 60 contacts the portion of thin film material 16 which covers the first open end 56 of the cell body 52. Since the pressure within the sample cup 50 is equalized by the second open end 58, the thin film material 16 which forms the sample surface, will remain consistently planar. The sample cup 50 is useful for applications analyzed in an air path or inert gas environment.

It will be understood that the present invention sample cups described herein are merely exemplary and that a person skilled in the art may make many variations and modifications to the described embodiment utilizing functionally equivalent components to those described. As such, variations and modifications, including differing physical geometries, proportions and materials are intended to be included within the scope of the invention as defined in the appended claims.

What is claimed is:

1. A cup assembly for holding a sample to be analyzed spectrochemically, consisting essentially of:

a first member forming a sample cell, said first member having a generally cylindrical wall extending between a first end and a second end thereof, a recess extending circumferentially about an outer surface of said wall of said first member, and an outwardly extending annular flange unitarily formed with said first end; and a second member for retaining a thin film placed across said second end of said first member, said second member having a generally cylindrical wall having a first end and a second, said second member cylindrical wall extending from said annular flange of said first member to said second end of said wall of said first member when said members are assembled together, wherein said first end of said second member cylindrical places the thin film against said annular flange of said first member, and a circumferentially extending bead projecting from an inner surface of said wall of said second member, said second member's bead adapted and constructed so as to fit within the recess of said first member;

wherein, when said first and second members are assembled to retain the thin film placed across said second end of said first member, said bead on said inner surface of said wall of second member slides along said outer surface of said wall of said first member and pulls an overhanging portion of the thin film down around an entire portion of said outer surface of said wall of said first member thereby progressively increasing the tautness of the thin film extending across the second end of the first member, the tautness of the film being maintained when said bead enters said recess and locks the first and second members together.

2. The cup assembly according to claim 1, wherein said first end of said first member is provided with an endwall, said endwall defining a centrally disposed reduced thickness region which is pierceable to permit atmospheric venting of said sealed cup.

3. The cup assembly according to claim 2, further comprising a substantially cylindrical wall extending from said annular flange, said end wall and said substantially cylindrical wall defining a reservoir for containing heat sensitive liquid samples.

4. The cup assembly according to claim 1, further comprising gripping means on an outer surface of said wall of said second member for providing a place to manually grip the second member during assembly of said cup.

5. The cup assembly according to claim 4, wherein said gripping means comprises an outwardly extending gripping flange.

6. A cup assembly for holding a sample to be analyzed spectrochemically, consisting essentially of:
a first member forming a sample cell, said first member having a generally cylindrical wall which extends between a first end and a second end thereof, and an outwardly extending annular flange unitarily formed with said first end;
a second member having a generally cylindrical wall having a first end and a second, said second member cylindrical wall extending from said annular flange of said first member to said second end of said wall of said first member when said members are assembled together, wherein said first end of said second member cylindrical wall places the thin film against said annular flange of said first member; and
film retaining means associated with said wall of each of said first and second members, for progressively increasing the tautness of a thin film placed across the second end of said first member,
wherein, when said first and second members are assembled to retain the thin film placed across said second end of said first member, said film retaining means associated with each of said walls pulls an overhanging portion of the thin film down around an entire outer surface of said wall of said first member thereby progressively increasing the tautness of the thin film extending across the second end of the first member.

7. The cup assembly according to claim 6, wherein said film retaining means comprises a recess extending circumferentially about an outer surface of said wall of said first member and a circumferentially extending bead projecting from an inner surface of said wall of said second member.

8. The cup assembly according to claim 6, wherein said film retaining means comprises a frustoconically shaped outer surface defined by said wall of said first member that converges continuously from said first end to said second end and a frustoconically shaped inner surface which converges continuously from a first end to a second end of said second member.

9. The cup assembly according to claim 6, wherein said first end of said first member is provided with an endwall, said endwall defining a centrally disposed reduced thickness region which is pierceable to permit atmospheric venting of said sealed cup.

10. The cup assembly according to claim 9, further comprising a substantially cylindrical wall extending from said annular flange, said end wall and said substantially cylindrical wall defining a reservoir for containing heat sensitive liquid samples.

11. The cup assembly according to claim 6, further comprising gripping means on an outer surface of said wall of said second member for providing a place to manually grip the second member during assembly of said cup.

12. The cup assembly according to claim 11, wherein said gripping means comprises an outwardly extending gripping flange.

13. A cup assembly for holding a sample to be analyzed spectrochemically, consisting essentially of:
a first member forming a sample cell, said first member having a generally cylindrical wall which extends between a first end and a second end thereof, and an outwardly extending annular flange unitarily formed with said first end;
a second member having a generally cylindrical wall having a first end and a second, said second member cylindrical wall extending from said annular flange of said first member to said second end of said wall of said first member when said members are assembled together, wherein said first end of said second member cylindrical wall places the thin film against said annular flange of said first member; and
gripping means on an outer surface of said wall of said second member for providing a place to manually grip the second member during assembly of said cup.

14. The cup assembly according to claim 13, wherein said gripping means comprises an outwardly extending gripping flange.

15. The cup assembly according to claim 13, further comprising film retaining means associated with said wall of each of said first and second members, for progressively increasing the tautness of a thin film placed across the second end of said first member wherein, when said first and second members are assembled to retain the thin film placed across said second end of said first member, said film retaining means associated with each of said walls pulls an overhanging portion of the thin film down around said wall of said first member thereby progressively increasing the tautness of the thin film extending across the second end of the first member.

16. The cup assembly according to claim 15, wherein said film retaining means comprises a recess extending circumferentially about an outer surface of said wall of said first member and a circumferentially extending bead projecting from an inner surface of said wall of said second member.

17. The cup assembly according to claim 15, wherein said film retaining means comprises a frustoconically shaped outer surface defined by said wall of said first member that converges continuously from said first end to said second end and a frustoconically shaped inner surface which converges continuously from a first end to a second end of said second member.

18. The cup assembly according to claim 13, wherein said first end of said first member is provided with an endwall, said endwall defining a centrally disposed reduced thickness region which is pierceable to permit atmospheric venting of said sealed cup.

19. The cup assembly according to claim 18, further comprising a substantially cylindrical wall extending from said annular flange, said end wall and said substantially cylindrical wall defining a reservoir for containing heat sensitive liquid samples.

20. The cup assembly according to claim 15, wherein said film retaining means comprises:

a frustoconically shaped outer surface defined by said wall of said first member that converges continuously from said first end to said second end, said outer surface including a recess extending circumferentially thereabout; and a frustoconically shaped inner surface which converges continuously from a first end to a second end of said second member, said inner surface including a circumferentially extending bead projecting therefrom.

* * * * *

UNITED STATES PATENT AND TRADEMARK OFFICE
CERTIFICATE OF CORRECTION

PATENT NO.        : 5,630,989
APPLICATION NO.   : 08/696104
DATED             : May 20, 1997
INVENTOR(S)       : Monte J. Solazzi Page 1 of 1

It is certified that error appears in the above-identified patent and that said Letters Patent is hereby corrected as shown below:

Col. 1, lines 4-9 DELETE

"This is a continuation of application Ser. No. 08/440,644, filed on May 15, 1995, entitled METHOD AND APPARATUS FOR TRIMLESS SAMPLE CUP USED IN X-RAY SPECTROSCOPY now abandoned which is a Continuation-in-part of prior application Ser. No. 08/292,058, filed on Aug. 17, 1994, now 5,451,375, issued Sep. 19, 1995."

TO:

--This is a continuation of application Ser. No. 08/440,644, filed on May 15, 1995, entitled METHOD AND APPARATUS FOR TRIMLESS SAMPLE CUP USED IN X-RAY SPECTROSCOPY now abandoned which is a continuation of prior application Ser. No. 08/292,058, filed on Aug. 17, 1994, now 5,451,375, issued Sep. 19, 1995, which is a continuation of Application No. 08/010,555, filed on Jan. 28, 1993, now abandoned.--

Signed and Sealed this

Eighth Day of August, 2006

JON W. DUDAS
*Director of the United States Patent and Trademark Office*

(12) EX PARTE REEXAMINATION CERTIFICATE (9932nd)
United States Patent
Solazzi

(10) Number: US 5,630,989 C1
(45) Certificate Issued: Nov. 12, 2013

(54) APPARATUS FOR TRIMLESS SAMPLE CUP USED IN X-RAY SPECTROSCOPY

(75) Inventor: Monte J. Solazzi, Jupiter, FL (US)

(73) Assignee: Chemplex Industries, Inc., Palm City, FL (US)

Reexamination Request:
No. 90/012,380, Jun. 29, 2012

Reexamination Certificate for:
Patent No.: 5,630,989
Issued: May 20, 1997
Appl. No.: 08/696,104
Filed: Aug. 13, 1996

Certificate of Correction issued Aug. 8, 2006

Related U.S. Application Data

(63) Continuation of application No. 08/440,644, filed on May 15, 1995, now abandoned, which is a continuation of application No. 08/292,058, filed on Aug. 17, 1994, now Pat. No. 5,451,375.

(51) Int. Cl.
*B01L 3/00* (2006.01)
*G01N 23/20* (2006.01)
*G01N 23/22* (2006.01)

(52) U.S. Cl.
USPC .......................................... 422/557; 422/566

(58) Field of Classification Search
None
See application file for complete search history.

(56) References Cited

To view the complete listing of prior art documents cited during the proceeding for Reexamination Control Number 90/012,380, please refer to the USPTO's public Patent Application Information Retrieval (PAIR) system under the Display References tab.

*Primary Examiner* — Pia Tibbits

(57) ABSTRACT

A sample receptacle for retaining a sample that is to be subjected to spectrochemical analysis. The sample receptacle includes a tubular body having at least one open end and a tapered exterior wall. A sheet of thin film material having peripheral edges is disposed across the open end of the tubular body. A generally annular collar, having an interior wall tapered at an angle supplemental to the taper of the interior wall, is disposed around the tubular body. As the annular collar is placed around the tubular body, the tapered exterior wall of the tubular body creates an interference fit with the tapered interior wall of the annular collar. The tapered surfaces of the tubular body and the annular collar engage the sheet of thin film material and pull the sheet of thin film material taut over the open end of the tubular body. The annular collar is sized to engage the entire length of the exterior wall of the tubular body. The portions of thin film material not covering the open end of the tubular body, including the peripheral edges of the thin film material are compressed between the tapered exterior wall of the tubular body and the tapered inside wall of the annular collar. As such, the sample receptacle can be handled without having to trim extraneous thin film material from the sides of the tubular body.

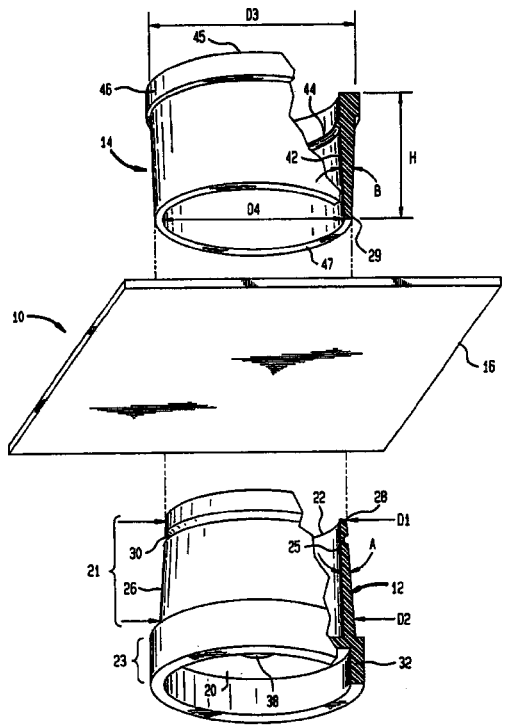

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, line 66 to Column 3, line 21:

The present invention is a sample receptacle for retaining a sample that is to be subjected to spectrochemical analysis. The present invention sample receptacle includes a tubular body having at least one open end and a tapered exterior wall. A sheet of thin film material having peripheral edges is disposed across the open end of the tubular body. A generally annular collar, having an interior wall tapered at an angle supplemental to the taper of the interior wall, is disposed around the tubular body. As the annular collar is placed around the tubular body, the tapered exterior wall of the tubular body creates an interference fit with the tapered interior wall of the annular collar. The tapered surfaces of the tubular body and the annular collar engage the sheet of thin film material and pull the sheet of thin film material taut over the open end of the tubular body. The annular collar is sized to engage the entire length of the exterior wall of the tubular body. The portions of thin film material not [coveting] *covering* the open end of the tubular body, including the peripheral edges of the thin film material, are compressed between the tapered exterior wall of the tubular body and the tapered inside wall of the annular collar. As such, the sample receptacle can be handled without having to trim extraneous thin film material from the sides of the tubular body.

Column 5, lines 25-38:

As mentioned, the interference fit between the annular collar 14 and the cell body 12 occurs over the entire length of the tapered surfaces. Any thin film material 16 not [coveting] *covering* the open end 22 of the cell body 12 is compressed between the outside wall 26 of the sample retaining region 21 and the interior wall 42 of the annular collar 14. Provided an appropriate length of thin film material 16 is initially used, none of the thin film material 16 will extend beyond the length of the annular collar 14. Thus, the step of having to trim extraneous portions of thin film material 16 away from the exterior of the sample cup 10 is eliminated. Use of the sample cup 10 with the one-piece annular collar 14 greatly simplifies sample preparation since the number of operational steps are reduced.

AS A RESULT OF REEXAMINATION, IT HAS BEEN DETERMINED THAT:

Claims 1-20 are cancelled.

New claims 21-38 are added and determined to be patentable.

21. *A cup assembly for holding a sample to be analyzed spectrochemically, consisting essentially of:*

*a first member forming a sample cell, said first member having a generally cylindrical wall which extends between a first end and a second end thereof, and an outwardly extending annular flange unitarily formed with said first end;*

*a second member having a generally cylindrical wall having a first end and a second end, said second member cylindrical wall extending from said annular flange of said first member to said second end of said wall of said first member when said members are assembled together, wherein said first end of said second member cylindrical wall places the thin film against said annular flange of said first member; and*

*film retaining means associated with said wall of each of said first and second members, said film retaining means comprising a frustoconically shaped outer surface defined by said wall of said first member that converges continuously from said first end to said second end and a frustoconically shaped inner surface which converges continuously from a first end to a second end of said second member,*

*wherein, when said first and second members are assembled to retain the thin film placed across said second end of said first member, said film retaining means associated with each of said walls pulls an overhanging portion of the thin film down around an entire outer surface of said wall of said first member thereby progressively increasing the tautness of the thin film extending across the second end of the first member.*

22. *The cup assembly according to claim 21, wherein said film retaining means further comprises a recess extending circumferentially about an outer surface of said wall of said first member and a circumferentially extending bead projecting from an inner surface of said wall of said second member.*

23. *The cup assembly according to claim 21, wherein said first end of said first member is provided with an endwall, said endwall defining a centrally disposed reduced thickness region which is pierceable to permit atmospheric venting of said sealed cup.*

24. *The cup assembly according to claim 23, further comprising a substantially cylindrical wall extending from said annular flange, said end wall and said substantially cylindrical wall defining a reservoir for containing heat sensitive liquid samples.*

25. *The cup assembly according to claim 21, further comprising gripping means on an outer surface of said wall of said second member for providing a place to manually grip the second member during assembly of said cup.*

26. *The cup assembly according to claim 25, wherein said gripping means comprises an outwardly extending gripping flange.*

27. *A cup assembly for holding a sample to be analyzed spectrochemically, consisting essentially of:*

*a first member forming a sample cell, said first member having a generally cylindrical wall which extends between a first end and a second end thereof, and an outwardly extending annular flange unitarily formed with said first end;*

*a second member having a generally cylindrical wall having a first end and a second end, said second member cylindrical wall extending from said annular flange of said first member to said second end of said wall of said first member when said members are assembled together, wherein said first end of said second member cylindrical wall places the thin film against said annular flange of said first member;*

*film retaining means associated with said wall of each of said first and second members, said film retaining means comprising a frustoconically shaped outer surface defined by said wall of said first member that converges* continuously from said first end to said second end and a frustoconically shaped inner surface which converges continuously from a first end to a second end of said second member; and gripping means on an outer surface of said wall of said second member for providing a place to manually grip the second member during assembly of said cup, wherein, when said first and second members are assembled to retain the thin film placed across said second end of said first member, said film retaining means associated with each of said walls pulls an overhanging portion of the thin film down around said wall of said first member thereby progressively increasing the tautness of the thin film extending across the second end of the first member.

28. The cup assembly according to claim 27, wherein said gripping means comprises an outwardly extending gripping flange.

29. The cup assembly according to claim 27, wherein said film retaining means further comprises a recess extending circumferentially about an outer surface of said wall of said first member and a circumferentially extending bead projecting from an inner surface of said wall of said second member.

30. The cup assembly according to claim 27, wherein said first end of said first member is provided with an endwall, said endwall defining a centrally disposed reduced thickness region which is pierceable to permit atmospheric venting of said sealed cup.

31. The cup assembly according to claim 30, further comprising a substantially cylindrical wall extending from said annular flange, said endwall and said substantially cylindrical wall defining a reservoir for containing heat sensitive liquid samples.

32. A cup assembly for holding a sample to be analyzed spectrochemically, consisting essentially of:

a first member forming a sample cell, said first member having a generally cylindrical wall which extends between a first end and a second end thereof, and an outwardly extending annular flange unitarily formed with said first end;

a second member having a generally cylindrical wall having a first end and a second end, said second member cylindrical wall extending from said annular flange of said first member to said second end of said wall of said first member when said members are assembled together, wherein said first end of said second member cylindrical wall places the thin film against said annular flange of said first member;

film retaining means associated with said wall of each of said first and second members, said film retaining means comprising a frustoconically shaped outer surface defined by said wall of said first member that converges continuously from said first end to said second end, said outer surface including a recess extending circumferentially thereabout; and a frustoconically shaped inner surface which converges continuously from a first end to a second end of said second member, said inner surface including a circumferentially extending bead projecting therefrom; and gripping means on an outer surface of said wall of said second member for providing a place to manually grip the second member during assembly of said cup, wherein, when said first and second members are assembled to retain the thin film placed across said second end of said first member, said film retaining means associated with each of said walls pulls an overhanging portion of the thin film down around said wall of said first member thereby progressively increasing the tautness of the thin film extending across the second end of the first member.

33. A trim less cup assembly, comprising:

a first member forming a sample cell, said first member having a generally cylindrical wall which extends between a first end and a second end thereof, and an outwardly extending annular flange unitarily formed with said first end;

a second member having a generally cylindrical wall having a first end and a second end, said second member cylindrical wall extending from said annular flange of said first member to said second end of said wall of said first member when said members are assembled together, wherein said first end of said second member cylindrical wall places the thin film against said annular flange of said first member; and film retaining means associated with said wall of each of said first and second members, said film retaining means comprising a frustoconically shaped outer surface defined by said wall of said first member that converges continuously from said first end to said second end and a frustoconically shaped inner surface which converges continuously from a first end to a second end of said second member, wherein, when said first and second members are assembled to retain the thin film placed across said second end of said first member, said film retaining means associated with each of said walls pulls an overhanging portion of the thin film down around an entire outer surface of said wall of said first member thereby progressively increasing the tautness of the thin film extending across the second end of the first member, and compressing the thin film of material between said walls, thereby eliminating the need to trim extraneous film from an assembled cup.

34. The trimless cup assembly according to claim 33, wherein said film retaining means further comprises a recess extending circumferentially about an outer surface of said wall of said first member and a circumferentially extending bead projecting from an inner surface of said wall of said second member.

35. The trimless cup assembly according to claim 33, wherein said first end of said first member is provided with an endwall, said endwall defining a centrally disposed reduced thickness region which is pierceable to permit atmospheric venting of said sealed cup.

36. The trimless cup assembly according to claim 33, further comprising a substantially cylindrical wall extending from said annular flange, said endwall and said substantially cylindrical wall defining a reservoir for containing heat sensitive liquid samples.

37. The trimless cup assembly according to claim 33, further comprising gripping means on an outer surface of said wall of said second member for providing a place to manually grip the second member during assembly of said cup.

38. The trimless cup assembly according to claim 37, wherein said gripping means comprises an outwardly extending gripping flange.

* * * * *